United States Patent [19]

Pearson et al.

[11] 4,231,362
[45] Nov. 4, 1980

[54] ANESTHESIA VENTILATION SYSTEM

[75] Inventors: Robert M. Pearson, 11685 Spicer Dr., Plymouth, Mich. 48170; A. Edwin Weninger, Los Alamitos, Calif.

[73] Assignee: Robert M. Pearson, Plymouth, Mich.

[21] Appl. No.: 947,946

[22] Filed: Oct. 2, 1978

[51] Int. Cl.$^3$ ............................................. A61M 16/00
[52] U.S. Cl. .......................... 128/205.15; 128/205.24
[58] Field of Search ............... 128/145.8, 145.6, 145.7, 128/145.5, 202, 188, 205.15

[56] References Cited
U.S. PATENT DOCUMENTS

| | | | |
|---|---|---|---|
| 2,592,694 | 4/1952 | Heidbrink | 128/202 X |
| 2,737,176 | 3/1956 | Fox | 128/145.8 |
| 3,256,876 | 6/1966 | Elam | 128/145.8 |
| 3,473,531 | 10/1969 | Tatham | 128/202 |
| 3,537,450 | 11/1970 | Fox | 128/145.6 |
| 3,973,564 | 8/1976 | Carden | 128/145.6 X |

*Primary Examiner*—Henry J. Recla
*Attorney, Agent, or Firm*—John A. Waters

[57] ABSTRACT

An anesthesia ventilation system for controlling gas flow through a patient breathing circuit by the inflation and deflation of a bellows that is outwardly expandable in a predetermined direction comprises a relief valve mounted in an outwardly expandable portion of the bellows, with the valve being biased to a normally closed position but being openable by an external pressure applied against the valve. A valve actuating member mounted in the bellows canister top plate in an adjustable position relative to the bellows engages and opens the valve and relieves the pressure in the bellows after the bellows has expanded outwardly a predetermined distance. The engagement of the valve actuating member with the valve also serves to block further outward expansion of the bellows. This limits the volume of gas contained in the bellows to a predetermined maximum amount.

11 Claims, 3 Drawing Figures

ANESTHESIA VENTILATION SYSTEM

BACKGROUND OF THE INVENTION

1. Field of the Invention

The present invention relates to an anesthesia ventilation system for assisting or controlling patient breathing and more particularly to a pressure relief and volume control valve mechanism incorporated in an expandable bellows in an anesthesia system.

2. Description of the Prior Art

An anesthesia ventilator system is used to maintain adequate ventilation and better anesthesia control during surgery. An anesthesia ventilation system typically includes an expandable bellows that is connected to a patient breathing circuit, with patient breathing being controlled by the controlled expansion and contraction of the bellows. Typically, the bellows is housed in a closed chamber or canister, and a mechanical pressure control device controls the pressure in the canister so as to cause inflation and of the bellows.

A ventilator system used for anesthesia administration also can be used for other gas balance breathing systems, such as in an intensive care gas ventilator system. As used herein the term "anesthesia ventilator system" shall include such other systems involving a continuous flow of gas into a closed or semiclosed system.

In using any constant flow anesthesia system to assist patient breathing, it is important that pressure not be allowed to build up in the system so as to impair patient breathing. Similarly, it is important that the volume of gas contained in the bellows be limited to a predetermined amount so that forced inhalation does not exceed the patient's lung capacity. These controls are particularly necessary when an anesthesia ventilator device is used to control patient breathing in veterinary medicine, wherein the lung capacities of small animals are much smaller than those of humans and vary widely among different animals. Without proper control of ventilation pressure and volume, the administration of anesthesia to a small animal can easily result in cardiopulmanary complications.

In conventional anesthesia apparatus, it is customary to include a relief valve in the patient breathing circuit to limit pressure build up in that circuit. However, when a ventilator is used to control patient breathing, the operation of such a relief valve does not provide satisfactory pressure control in the system.

It is an object of the present invention to provide an improved anesthesia system particularly adapted to inhalation anesthesia of small animals that provides increased pressure and volume control by means of a simple and inexpensive control mechanism. Another object of the present invention is to make such a control apparatus compatible with a positive end expiratory pressure system.

SUMMARY OF THE INVENTION

The present invention comprises an improvement in an anesthesia ventilation system wherein gas flow through a patient breathing circuit is controlled by inflation and deflation of a bellows that is outwardly expandable in a predetermined direction. The improvement comprises a relief valve mechanism mounted in an outwardly expandable portion of the bellows, with the relief valve being biased to a normally closed position but being openable by external pressure applied against the valve. A valve actuating member mounted in the bellows canister top plate in an adjustable position relative to the bellows is positioned and constructed so as to engage and open the valve after the bellows has expanded outwardly a predetermined distance. The opening of the valve permits gas flow out of the bellows to relieve the pressure in the bellows. The engagement of the valve member with the valve also serves to block further outward expansion of the bellows. This limits the volume of gas contained in the bellows to a predetermined maximum amount.

The relief valve is an umbrella valve mounted in an opening in an upper surface of an upwardly expandable bellows, with the relief valve being normally biased in its closed position. The valve actuating member is mounted above the relief valve in an adjustable predetermined position, so that the relief valve engages the actuating member after it has moved upwardly a predetermined distance. Engagement between the actuating member and the relief valve blocks further expansion of the bellows and opens the valve to relieve the pressure in the bellows.

The umbrella valve also serves as an inspiratory relief valve in the event that the patient initiates an inspiratory effort when the bellows is completely collapsed. In such a case, the relief valve opens and entrains ambient air.

A rod extends upwardly from the umbrella valve housing in the upper surface of the bellows. The valve actuating member is a tubular member or sleeve surrounding the upwardly extending rod. The rod acts as an alignment device for the bellows to assure that its upward movement is in a vertical path and that the top surface of the bellows remains horizontal. This is important for proper movement of the bellows and for calculating the volume of gas being delivered to the patient breathing system.

The valve mechanism of the present invention is also compatible with the creation of an atmospheric or slightly positive pressure at the end of exhalation, the clinical term for which is positive end expiratory pressure ("P.E.E.P."). This pressure can be altered by means of adjustment of the umbrella valve mechanism.

These and other features and advantages of the present invention will hereinafter appear, and, for purposes of illustration, but not of limitation, a preferred embodiment of the invention is described in detail below and shown in the appended drawings.

DETAILED DESCRIPTION OF PREFERRED EMBODIMENt

Figure 1:
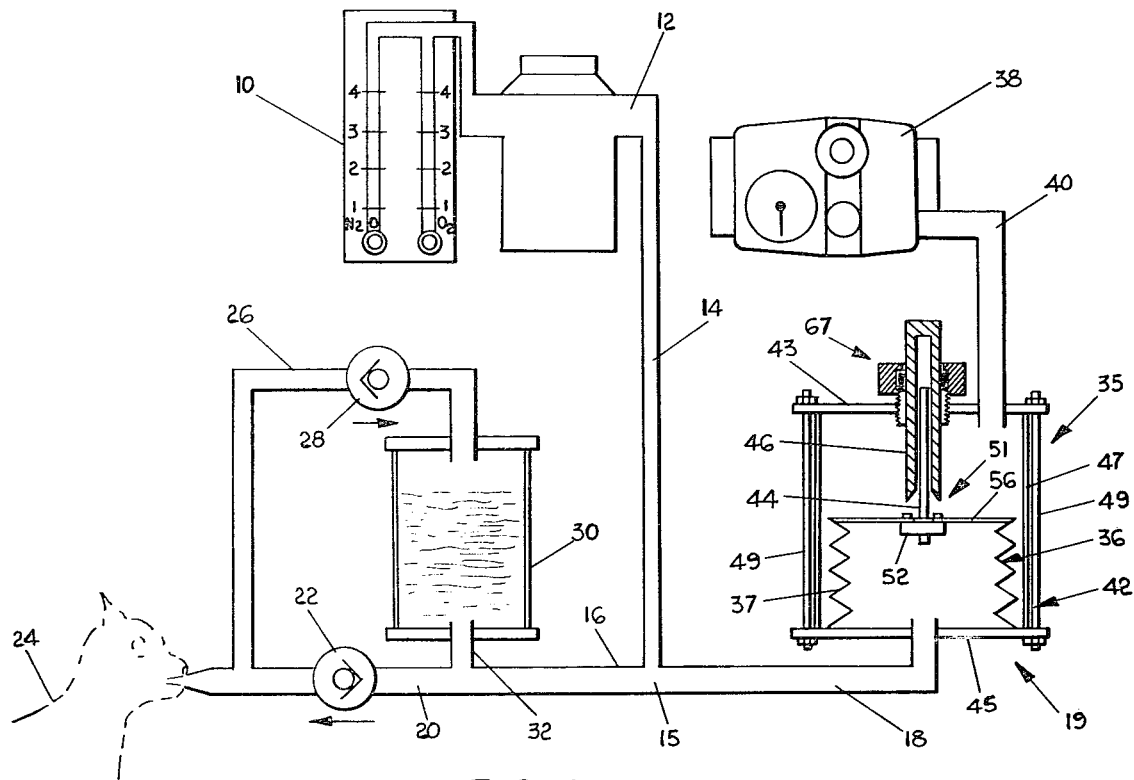
FIG. 1 is a schematic diagram showing the use of the anesthesia apparatus of the present invention in connection with a small animal anesthesia ventilation system.

Referring now to the drawings, in a conventional anesthesia device in which a ventilator or forced breathing apparatus is employed, oxygen and nitrous oxide are mixed in a nixing device 10. The mixture is then passed through a vaporizer 12, wherein anesthetic is added to the mixture. The mixture passes through a conduit 14 to a T connection 15, one leg 16 of which leads to the animal being anesthesized and the other leg 18 of which leads to a bellows apparatus 19 for controlling or assisting animal breathing during anesthesia.

Leg 16 branches into a conduit 20 which leads through a one-way valve 22 to the animal 24. A return path 26 leads through another one-way valve 28 to a filter 30, which absorbs carbon dioxide from exhaled air. The exhaled air then passes back to conduit 16 through conduit 32, where it can repeat the cycle through the animal, picking up additional oxygen nitrous oxide and anesthesia from line 14. This circuit is commonly referred to as the patient breathing circuit.

Ventilator apparatus 19 either assists or controls animal breathing during anesthesia. This device includes a bellows assembly 35 and a respirator 38, which is connected to the bellows assembly through a conduit 40 to control the inflation and deflation of the bellows.

Bellows assembly 35 includes an upwardly expandable bellows 36 mounted in an enclosed and sealed chamber or canister 42, which includes upper and lower plates 43 and 45 and a transparent cylindrical sleeve 47 compressed between the plates by tie rods 49 spaced around the periphery of the plates. Respirator 38, which is a conventionally available unit, controls the pressure in the canister surrounding the bellows. When the pressure in the canister is increased, this causes the bellows to deflate, thus initiating an inspiration cycle for the patient. Conversely, when the respirator causes a decrease of pressure in the canister, the bellows is permitted to inflate. A preferred respirator for use in connection with the present invention is a Bird*, Mark Seven respirator unit. This unit can be adapted to *control* patient breathing, that is, operate on a timed control sequence where the patient is forced to breathe in accordance with the time sequence. Alternatively, it can be operated to merely *assist* patient breathing, in which case, the initiation of an inspiratory effort by the patient triggers the respirator to deflate the bellows. These functions can be accomplished in a conventional manner.
*Registered Trademark Bellows 36 is mounted at the bottom of canister 42, with the interior of the bellows being in communication with conduit 18 through an outlet at the bottom of the container. The bellows includes vertical side walls 37 comprising flexible material folded in accordian fashion, so that the side walls are vertically expandable as the bellows is inflated. The bellows also includes a top surface 56 that is formed of a flat rigid material. Top surface 56 moves upwardly and downwardly in a horizontal plane as the bellows expands and contracts.

Figures 2, 3:
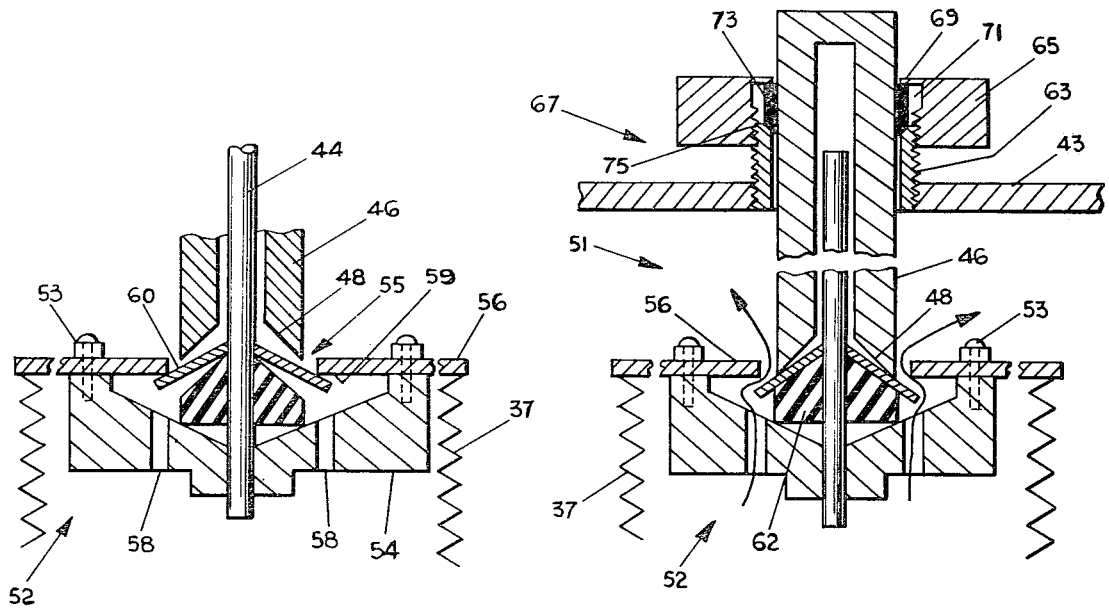
FIG. 2 is a partially broken cross-sectional view showing the relief valve mechanism of the present invention in its normally closed position.
FIG. 3 is a partially broken cross-sectional view showing the relief valve mechanism of the present invention having been moved to its open position by the valve actuating member.

The bellows also includes an automatic pressure relief mechanism 51, as shown in FIGS. 2 and 3. Since the anesthesia apparatus provides a continuously recycling oxygen supply to the patient, additional gas added to the cycle would normally increase the gas pressure in the system, thus impairing ventilation of the patient. In order to relieve gas pressure in the system, a gas relief valve mechanism 52 is incorporated in an opening 55 in the upper surface of the bellows. Relief valve 52 includes a mounting bracket 54 attached to the underside of the upper surface of the bellows by threaded fasteners 53 or the like. A cylindrical rod 44 is held in place in a central opening in bracket 54 and extends upwardly through opening 55 in the upper surface of the bellows in a vertical direction. A plurality of openings 58 are formed downwardly through bracket 54 so as to provide fluid communication between the interior of the bellows and the exterior of the bellows through openings 58 and opening 55.

A valve member 60 comprising a flexible, umbrella shaped diaphram formed of rubber or the like is mounted on the underside of opening 55 on rod 44. The diaphram is normally biased in a closed position so that it covers the opening in the upper surface and engages a valve seat 59 formed by the edges of upper surface 56 surrounding opening 55. Pressure exerted on the diaphram from the inside of the bellows urges the diaphram against upper surface 56 and prevents gas from escaping from the bellows. However, when the diaphram is moved downwardly away from top 56, (as shown in FIG. 3) gas is permitted to escape from the bellows around the outer edges of the diaphram. An expansion blocking or motion limiting device 62 (which may be an ordinary faucet seal) positioned on rod 44 below diaphram 60 limits the downward movement of the diaphram (as shown in FIG. 3) so that gas can escape from the bellows at a limited rate. The motion limiting device has a conically shaped upper surface that is formed at a sharper angle than the normal position of the umbrella valve member so that the umbrella valve member can be deflected downwardly a sufficient distance to open the valve before the valve member engages the upper surface of the motion limiting device. The motion limiting device and the diaphram are positioned such that the rate of gas flow through the open valve is limited, thus making it possible to maintain some pressure in the bellows even when the valve is open. This is desirable when the present invention is used in a positive end expiratory pressure (P.E.E.P.) system The relief valve mechanism is actuated by means of a valve actuating member 46 mounted in the top surface 43 of canister 42. Valve actuating member 46 comprises a sleeve having a closed upper end and a vertical opening therein that engages and guides rod 44 so as to maintain the rod in vertical alignment. Maintenance of vertical alignment is important in calibrating volume measurements at various expansion positions of the bellows.

The lower end 48 of member 46 protrudes downwardly into the interior of canister 42 to a position above the upper surface of the bellows. Lower end 48 has an upwardly and inwardly tapered conical or beveled surface and is formed so that when the bellows expands upwardly into contact with the lower end 48 of valve actuating member 46, an edge of the lower end engages the relief valve around the periphery thereof and opens the relief valve by resiliently moving diaphram 60 downwardly, in the manner shown in FIG. 3. After diaphram 60 is moved downwardly into contact with motion limiting device 62, further upward movement of the bellows is blocked, thus preventing further volume expansion of the bellows.

Valve actuating member 46 is adjustably held in position in an opening in upper surface or plate 43 of the canister by means of an adjustable clamping mechanism 67. Adjustable clamping mechanism 67 comprises an externally threaded sleeve 63 that is screwed into a threaded opening in the top of the canister. An internally threaded nut 65 engages the threaded exterior of sleeve 63. An inwardly extending flange 69 on the upper surface of nut 63 encloses an open annular area 71 between nut 65 and valve actuating member 46. A compressable ring seal 73 formed of rubber of the like fits in space 71 between the nut and the valve actuating member. By threading nut 65 downwardly on sleeve 63, flange 69 axially compresses seal 73 and causes it to expand outwardly in a horizontal direction. This causes a resilient gripping engagement between seal 73 and member 46. This accomplishes two purposes. It seals the space between valve actuating member 46 and the opening in upper surface 43 of the canister, and at the same time holds the valve actuating member in a fixed vertical position with respect to the canister. A beveled upper surface 75 on sleeve 63 also urges seal 73 into clamping engagement with valve actuating member 46.

With the mounting mechanism formed in this manner, the position of valve actuating member 46 can be varied easily by loosening nut 65 and then sliding the valve actuating member upwardly or downwardly along rod 44. The nut is then retightened to hold the rod in any desired position.

With the apparatus of the present invention, the bellows is permitted to expand only a predetermined distance until the bellows comes in contact with valve actuating member 46. The valve actuating member then opens the flexible diaphram 60 relieving gas pressure in the bellows. At the same time the engagement between the valve actuating member and motion limiting device 62 prevents further upward expansion of the bellows. By adjusting the vertical position of valve actuating member 46, the maximum volume of the bellows can be carefully and easily adjusted, thus preventing overinflation of the bellows in excess of a patient's lung capacity. The release of gas pressure from the interior of the bellows prevents excess pressure build up in the patient beathing circuit.

In many ventilation devices, the bellows in positioned so as to be downwardly expandable. In the present invention, the bellows is upwardly expandable. This makes it possible for the bellows to function in a positive end expiratory pressure system. Such a system makes it possible to create positive end expiratory pressure if desired. This is considered to be a desirable situation at the present time. With an upwardly expanding bellows, there is always a slight pressure resisting bellows inflation and therefore resisting patient exhalation. The particular pressure employed can be adjusted (a factory adjustment) by adjusting the valve mechanism.

It should be understood that the foregoing is merely an exemplary embodiment of the present invention and that various changes and modifications may be made in the arrangements and details of construction of the present invention without departing from the spirit and scope of the present invention.

The embodiments of the invention in which an exclusive property or privilege is claimed are defined as follows:

1. In an anesthesia ventilator system wherein an inflatable bellows is enclosed in a sealed canister, with the interior of the bellows being in fluid communication with a patient breathing circuit and inflation and deflation of the bellows being controlled by a respirator in fluid communication with the portion of the interior of the canister surrounding the bellows, the respirator controlling inflation and deflation of the bellows by varying the pressure in the canister, the bellows being positioned for expansion in an upward direction during inflation, the improvement comprising:

a rod extending upwardly from the top of the bellows;

a sleeve mounted in the top of the canister and extending downwardly therefrom to a lower end, the sleeve having an elongated opening extending upwardly from the lower end, the opening being formed and positioned such that it mates with the rod on the bellows and constrains the rod to vertical movement as the bellows expands and contracts upwardly and downwardly, the sleeve including a valve actuating portion at the lower end; and valve means mounted in an opening in the upper surface of the bellows for permitting gas flow between the interior of the canister and the interior of the bellows, said valve means being resiliently biased in a normally closed position so as to block gas flow out of the bellows through said opening, the valve means being positioned for engagement with the valve actuating portion of the sleeve and being openable by engagement therewith after the bellows has expanded upwardly a predetermined distance, the opening of the valve means serving to relieve the internal gas pressure in the bellows.

2. An improvement according to claim 1 wherein the valve means is resiliently openable by an external force applied against the valve means such that the valve means opens to permit gas flow from the canister into the bellows when the pressure differential between the interior of the bellows and the interior of the canister reaches a predetermined level.

3. An improvement according to claim 2 wherein the predetermined pressure is such that if a patient inspiratory effort is initiated when the bellows is fully collapsed and there is at least atmospheric pressure in the canister, the valve means will open and will permit the patient to breath gas drawn from the canister through the valve and bellows to the patient breathing circuit.

4. An improvement according to claim 1 wherein the apparatus further includes expansion blocking means for stopping further upward movement of the bellows after the valve actuating portion of the sleeve has engaged and opened the valve means.

5. An improvement according to claim 4 wherein the expansion blocking means is the valve means, the valve means being movable through a limited distance in moving from a closed to an open position, the valve means thereafter resisting further movement, the engagement between the valve means and the valve actuating portion preventing further upward movement of the bellows.

6. An anesthesia ventilator according to claim 1 or 5 wherein the position of the sleeve in the top of the canister is vertically adjustable so as to permit the valve actuating portion thereof to engage the valve means at different expanded volumes of the bellows, the adjustment permitting control over the maximum volume of the bellows.

7. An improvement according to claim 1 wherein the valve means includes a valve member positioned on the underside of the opening in the upper surface of the bellows, with the valve member being resiliently biased upwardly to cover the opening, the valve actuating portion extending downwardly so as to engage the valve member and deflect it downwardly to an open position as the bellows expands upwardly.

8. An improvement according to claim 7 wherein the rod is attached to the upper surface of the bellows and is positioned so as to be extending upwardly through the opening, the valve member being a flexible, resilient member mounted on and surrounding the rod so as to resiliently cover the opening on the underside of the upper surface, the valve actuating portion of the sleeve being the lower end of the sleeve, the lower end being shaped such that it engages and opens the valve member when the bellows expands upward to a predetermined point.

9. An improvement according to claim 8 wherein the flexible member is a flexible umbrella member having a downwardly facing conical shape, with the lower end of the sleeve having an upwardly and inwardly tapered conical surface such that a lower edge of the sleeve engages the valve member around the circumference of the sleeve.

10. An improvement according to claim 9 and further comprising a motion limiting member mounted on the rod below the umbrella member, the motion limiting member limiting downward deflection of the umbrella member to a limited distance so as to limit the distance the valve is opened and prevent further downward penetration of the sleeve, the engagement between the sleeve and the motion limiting member serving to stop upward movement of the bellows.

11. An improvement according to claim 8 wherein:
the canister has a top positioned above the upper surface of the bellows, with the top having an opening therethrough; and
releasable gripping means is mounted in the opening, the releasable gripping means having a vertical opening therethrough that mates with the outer surface of the sleeve, a compressible, annular seal being positioned between the releasable gripping means and the sleeve, the gripping means further comprising a releasable seal compressing means for compressing the seal such that the seal is urged inwardly against the sleeve and resiliently seals the space between the gripping means and the sleeve, the engagement between the seal and the sleeve further serving to clamp the sleeve in its desired vertical position in the gripping means, the seal compressing means being releasable to permit vertical height adjustment of the sleeve.

* * * * *